(12) United States Patent
Kilburg

(10) Patent No.: US 11,298,300 B2
(45) Date of Patent: Apr. 12, 2022

(54) STABLE PICKERING-TYPE EMULSIONS

(71) Applicant: Ciella James LLC, New York, NY (US)

(72) Inventor: Denise Kilburg, New York, NY (US)

(73) Assignee: CIELLA JAMES LLC, New York, NY (US)

( * ) Notice: Subject to any disclaimer, the term of this patent is extended or adjusted under 35 U.S.C. 154(b) by 298 days.

(21) Appl. No.: 16/807,272

(22) Filed: Mar. 3, 2020

(65) Prior Publication Data

US 2021/0275411 A1 Sep. 9, 2021

(51) Int. Cl.
*A61K 8/06* (2006.01)
*A61K 8/34* (2006.01)
*A61K 8/60* (2006.01)
*A61K 8/36* (2006.01)

(52) U.S. Cl.
CPC ............. *A61K 8/06* (2013.01); *A61K 8/345* (2013.01); *A61K 8/361* (2013.01); *A61K 8/60* (2013.01); *A61K 2800/10* (2013.01)

(58) Field of Classification Search
CPC ........ A61K 8/06; A61K 8/64; A61K 2800/33; A61K 8/062; A61K 8/29; A61K 2300/00; A61K 8/064; A61K 2800/28; A61K 2800/413; A61K 36/28; A61K 36/73; A61K 8/345; A61K 8/9789; A61K 9/10; A61K 9/107; A61K 2800/412; A61K 8/0241; A61K 2800/524; A61K 8/9794; A61K 2800/654; A61K 8/19; A61K 8/22; A61K 8/25; A61K 8/27; A61K 2800/30; A61K 2800/41; A61K 2800/592; A61K 38/55; A61K 8/02; A61K 8/0204; A61K 8/60; A61K 8/66; A61K 8/732; A61K 8/8152; A61K 8/97; A61K 2800/10; A61K 2800/21; A61K 2800/612; A61K 2800/85; A61K 2800/87; A61K 2800/884; A61K 31/045; A61K 31/702; A61K 33/04; A61K 33/24; A61K 33/26; A61K 33/30; A61K 33/32; A61K 33/34; A61K 35/74; A61K 36/534; A61K 47/02; A61K 47/44; A61K 8/0279; A61K 8/044; A61K 8/20; A61K 8/34; A61K 8/36; A61K 8/361; A61K 8/365; A61K 8/44; A61K 8/463; A61K 8/466; A61K 8/4946; A61K 8/4966; A61K 8/498; A61K 8/4993; A61K 8/85; A61K 8/88; A61K 8/922; A61K 9/00; A61K 9/0014; A61K 9/0034; A61K 9/06; A61Q 17/04; A61Q 19/00; A61Q 7/02; A61Q 11/00; A61Q 15/00; A61Q 19/10; A61Q 1/02; A61Q 19/04; A61Q 1/04; A61Q 1/10; A61Q 19/002; A61Q 19/02; A61Q 1/06; A61Q 3/00; A61Q 3/02; A61Q 5/006; A61Q 5/02; A61Q 5/06; A61Q 5/12; A61Q 9/00; A61Q 17/005; A61Q 19/005; A61Q 19/007; A61Q 19/08; Y10S 514/937; Y10S 514/938; Y10S 514/939; Y10S 514/844; Y10S 514/848; Y10S 514/859
See application file for complete search history.

(56) References Cited

U.S. PATENT DOCUMENTS

2004/0071642 A1* 4/2004 Amalric ................ A61Q 19/00
424/59
2019/0374444 A1* 12/2019 Hutson .................... A61K 8/25

OTHER PUBLICATIONS

Dyab et al. "Non-aqueous olive oil-in-glycerin (o/o) Pickering emulsions: Preparation, characterization and in vitro aspirin release" Journal of Dispersion Science and Technology, vol. 39, Issue 6; pp. 1-13; see abstract in particular; Dec. 8, 2017 (Year: 2017).*

* cited by examiner

*Primary Examiner* — Audrea B Coniglio
(74) *Attorney, Agent, or Firm* — Arent Fox LLP

(57) ABSTRACT

The present disclosure provides stable Pickering-type emulsions comprising glycerin and oil, as well as methods of manufacturing the same. In some aspects, such emulsions further comprise magnesium stearate and a non-ionic surfactant as co-emulsifiers.

20 Claims, 3 Drawing Sheets

STABLE PICKERING-TYPE EMULSIONS

TECHNICAL FIELD

The disclosure generally relates to stable Pickering-type emulsions comprising glycerin and oil, as well as methods of manufacturing the same.

BACKGROUND

Emulsions are ubiquitous in many different fields including cosmetics, pharmaceutics, the food industry, and so on. Emulsions are systems which include two immiscible liquids that are held together either by surfactants (cationic, anionic, amphoteric, or non-ionic) as in traditional emulsions, or by solid particles (e.g., silica, clay, hydroxyapatite (Hap), and some organic particles) as in the case of Pickering-type emulsions. Surfactants are amphiphilic molecules that consist of a lipophilic (non-polar) tail and a hydrophilic (polar) head. When polar and non-polar substances are mixed, surfactants become absorbed at the interface between the two liquids and serve to decrease the surface and interfacial tension, thus stabilizing the emulsion by inhibiting the coalescence of the internal phase droplets. However, with surfactants, there exists a dynamic equilibrium at the interface with sorption/desorption at the interface leading to thermal instability over time.

Emulsions of glycerin and oil are significantly less stable than that of oil and water, which makes them less ubiquitous. However, there is renewed interest in making stable glycerin and oil emulsions, particularly in the cosmetic and pharmaceutical industries. For example, there has been a growing call for companies to become more sustainable as climate change is predicted to cause global water shortages. One way, is to reduce water in the process of making the products as well as decreasing water content of the product itself. Most skincare formulations are oil-in-water emulsions that contain significant amounts (e.g., 70%) of water. The inclusion of water in such formulations is problematic, as consumer products containing water must normally contain preservatives. Many consumers are concerned with the apparent toxicity of preservatives, specifically parabens and phenoxyethanol. Completely anhydrous glycerin and oil emulsions are therefore in high demand. However, using known methods, stable glycerin and oil emulsions can only be accomplished with the use of large percentages of added thickeners and/or waxes and thus are only be suitable for solid-like products such as lipsticks and balms.

SUMMARY OF VARIOUS ASPECTS

In view of the shortcomings of existing formulations for glycerin and oil emulsions, which are unable to maintain stability without incurring other undesirable aspects, there exists a need in the art for stable glycerin and oil emulsions manufactured without the use of large amounts of thickeners, for liquid and liquid-like (e.g., soft) emulsions for cosmetic application to the skin of the face and body, as well as for other uses. The present disclosure provides, in some aspects, formulations for Pickering-type emulsions comprising glycerin and oil (as well as emulsions comprising other polyols and oils), and magnesium stearate alone or in combination with sorbitan olivate as emulsifiers, which display enhanced stability. In some aspects, such formulations may advantageously be prepared without any preservatives, e.g., parabens or phenoxyethanol.

In the case of Pickering-type emulsions, surfactants are replaced by solid particles, usually colloids, that form a physical barrier between the two liquids at the interface which stabilizes the emulsion. These particles are strongly anchored at the interface and therefore do not suffer as much from the thermodynamic instability that plagues surfactants, resulting in a much more stable emulsion. In some aspects, the present disclosure provides a method of creating a Pickering-type emulsion using salts of fatty acids for the stabilization of glycerin-in-oil (g/o) and oil-in-glycerin (o/g) emulsions.

In a general aspect, the disclosure provides a Pickering-type emulsion, comprising: (a) a discontinuous internal phase, wherein the internal phase comprises a polyol in an amount of at least, at most, or about 5, 15, 25, 35, 45, 55, 65, 75, or 85% by weight of the entire emulsion (e.g., 15-35% by weight of the entire emulsion); (b) a continuous external oil phase, in an amount of at least, at most, or about 15, 25, 35, 45, 55, 65, 75, 85, or 95% by weight of the entire emulsion (e.g., 55-85% by weight of the entire emulsion); and (c) at least one emulsifier. In some aspects, the emulsifier comprises or consists of magnesium stearate.

In some aspects, the polyol is selected from the group consisting of ethylene glycol, propylene glycol, butylene glycol, hexylene glycol, sorbitol, and diethylene glycol. In some aspects, the polyol is glycerin.

In some aspects, the emulsion further comprises sorbitan olivate as a co-emulsifier. In some aspects, the only emulsifier in the composition is magnesium stearate. In some aspects, the only emulsifiers in the composition are magnesium stearate and sorbitan olivate. In some aspects, magnesium stearate is the only emulsifier present in the emulsion in an amount of at least 0.25, 0.50, 0.75, 1.00, 1.25, 1.50, or 2.00% by weight of the entire emulsion. In some aspects, the emulsion may comprise magnesium stearate in an amount of at least, at most, or about 0.25, 0.50, 0.75, 1.00, 1.25, 1.50, 1.75, 2.00, 2.25, 2.50, 2.75, 3.00, 3.25, 3.50, 3.75, 4.00 4.25, 4.50, 4.75 or 5.00% by weight of the entire emulsion (or at a concentration within a range bounded by any of these values). In still further aspects, the emulsion may comprise magnesium stearate in an amount of at least, at most, or about 6, 7, 8, 9, 10, 11, 12, 13, 14, 15, 16, 17, 18, 19, 20, 21, 22, 23, 24, or 25% by weight of the emulsion (or at a concentration within a range bounded by any of these values). In still further aspects, the emulsion may comprise magnesium stearate in an amount of at least, at most, or about 25, 30, 35, 40, 45, 50, 55, 60, 65, 70, 75, 80, 85, 90 or 95% by weight of the emulsion (or at a concentration within a range bounded by any of these values).

In some aspects, the emulsion may further comprise sorbitan olivate in an amount of at least, at most, or about 0.25, 0.50, 0.75, 1.00, 1.25, 1.50, 1.75, 2.00, 2.25, 2.50, 2.75, 3.00, 3.25, 3.50, 3.75, 4.00, 4.25, 4.50, 4.75, 5.00% by weight of the entire emulsion (or at a concentration within a range bounded by any of these values). In still further aspects, the emulsion may comprise sorbitan olivate in an amount of at least, at most, or about 6, 7, 8, 9, 10, 11, 12, 13, 14, 15, 16, 17, 18, 19, 20, 21, 22, 23, 24, or 25% by weight of the emulsion (or at a concentration within a range bounded by any of these values). In still further aspects, the emulsion may comprise sorbitan olivate in an amount of at least, at most, or about 25, 30, 35, 40, 45, 50, 55, 60, 65, 70, 75, 80, 85, 90 or 95% by weight of the emulsion (or at a concentration within a range bounded by any of these values). In some aspects, the emulsions described herein may be completely anhydrous and/or may be formulated without any preservatives.

In some aspects, the magnesium stearate and/or the sorbitan olivate may be localized to the interface between the discontinuous internal phase and the continuous external phase of the emulsion. In some aspects, substantially all of the magnesium stearate and/or the sorbitan olivate present in the emulsion may be localized to this interface (e.g., the magnesium stearate may form a layer of solid particles at this liquid-liquid interface, forming the Pickering emulsion). In some aspects, at least 50, 60, 70, 80, 90, or 95 wt. % of the magnesium stearate and/or the sorbitan olivate present in the emulsion may be localized to this interface. In some aspects, the magnesium stearate and/or the sorbitan olivate may form a layer at the liquid-liquid interface which stabilizes the emulsion by reducing or preventing coalescence and/or flocculation.

In some aspects, the discontinuous internal phase comprises droplets having an average diameter of 10-40 μm. In some aspects, the droplets are spherical or substantially spherical. In some aspects, when emulsions are prepared accorded to the present disclosure using magnesium stearate as the emulsifier, the droplets may have an average diameter of <1 μm, e.g., about, at least or approximately 100, 200, 300, 400, 500, 600, 700, 800, 900 nm (or a size within a range bounded by any of these values). In some aspects, when emulsions are prepared accorded to the present disclosure using (1) sorbitan olivate as the emulsifier or (2) magnesium stearate and sorbitan olivate as co-emulsifiers, the droplets may have an average diameter of 10-30 μm, e.g., about, at least or approximately 10, 11, 12, 13, 14, 15, 16, 17, 18, 19, 20, 21, 22, 23, 24, 25, 26, 27, 28, 29, or 30 μm (or a size within a range bounded by any of these values).

In some aspects, the emulsion is stable for at least 24, 36, 48, 60, or 72 hours at 60° C. In some aspects, the emulsion is stable for at least 1, 2, 3, 4, 5, or 6 months at room temperature. In some aspects, stability is evaluated based on the degree of phase separation and a stable emulsion displays no visible phase separation by the aforementioned time-points.

In some aspects, the disclosure provides cosmetic compositions which comprise a Pickering-type emulsion as described herein. Such cosmetic compositions may, e.g., be liquid or semi-liquid, and may comprise additional components known to be useful in cosmetic formulations (fragrances, pigments, moisturizing agents, etc.)

The aforementioned examples are non-limiting. Additional aspects will be readily apparent to one of skill in light of the totality of the disclosure.

DETAILED DESCRIPTION OF VARIOUS ASPECTS

Figure 1:
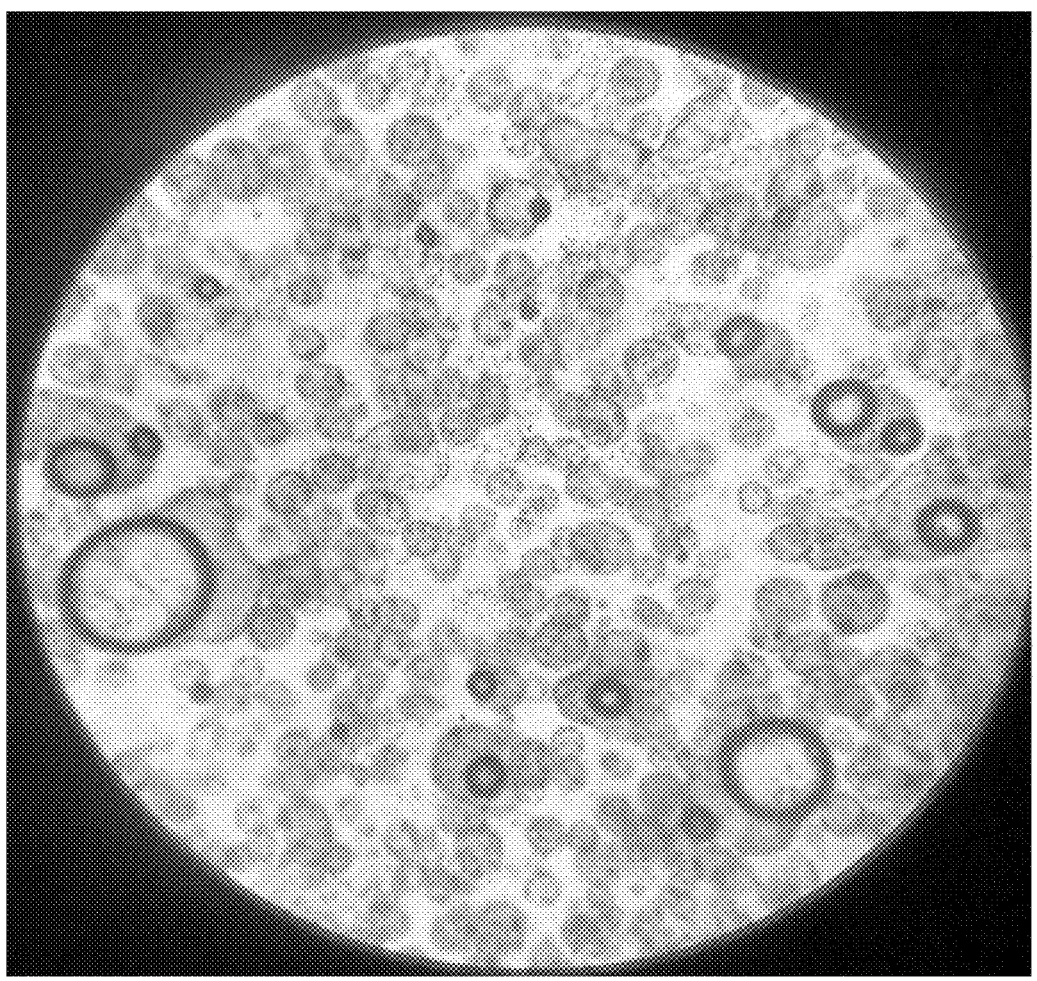
FIG. 1 is a microscope image of Formulation A with 3.0% (w/w) sorbitan olivate as the sole emulsifier, viewed at 1000× magnification. The diameter of the field of view is approximately 180 μm.

Glycerin is widely used in cosmetics as well as in pharmaceutical formulations, mainly as a humectant. Glycerin is a polyhydric alcohol that is also used widely for: (1) botanical extracts, due to the fact that it is a non-denaturing alcohol; (2) as a vehicle for allergens in allergy testing, due to its non-allergenic nature; and (3) as a wound-healing pharmaceuticals due to its hydroscopic properties and bacteriostatic nature. Most glycerin-in-oil emulsions in cosmetics are applied to lipsticks and lip-based products, although such formulations are typically wax-based solids containing a large percentage of thickening agents such as beeswax, candelillia wax, etc. For example, U.S. Pat. Nos. 6,090,386 and 6,325,995, which are incorporated herein in their entirety, describe such glycerin-in-oil emulsions that are wax-based with a solid consistency.

Glycerin-in-oil and oil-in-glycerin emulsions that have a more fluid consistency are plagued with thermal instability. This is in part due to the large density difference between the internal glycerin phase (1.26 g/cm3) and external oil phase (0.93 g/cm3) and vice-versa. For example, U.S. Pat. No. 4,254,104 describes a failure of prior attempts to make glycerin-in-oil emulsions and U.S. Pat. No. 8,302,774 achieves such emulsions only by requiring the use of a combination of trihydroxystearin and 12-hydroxystearic acid to thicken and stabilize the glycerin-in-oil emulsions. The entire contents of each of these patents is incorporated herein in its entirety. Pursuant to Stokes' Law, three variables control stability: (1) droplet size of the internal phase, (2) the difference in density of the two phases, and (3) the viscosity of the external phase. Prior attempts to stabilize glycerin-in-oil emulsions based on Stokes' Law have thus far failed to efficiently resolve this concern. As noted above, e.g., the inclusion of thickeners as a stabilizing agent results in a solid-like product that typically cannot be used in applications which require a liquid or semi-liquid consistency.

Glycerin-in-oil and oil-in-glycerin emulsions must pass cosmetic stability testing in order to be sold in most venues. Typical cosmetic stability testing usually includes extreme stresses in the areas of temperature, UV light, and humidity. In the case of temperature, while there is no set standard, tests usually include subjecting the product to temperatures of 45° C. for 2, 4, and 8 weeks. If the product does not appear to have any objectionable change, the stability is assessed to be 3 months, 6 months, and 12 months, respectively. Tests can also be run at different temperatures, e.g. 45° C., 50° C. and 60° C., or for longer durations of time.

In some aspects, the present disclosure provides compositions comprising glycerin-in-oil or oil-in-glycerin emulsions that have markedly improved stability with respect to the time before deterioration occurs (e.g., phase separation) and exposure to high temperatures (which normally hasten degradation).

In one aspect, the present disclosure also provides compositions comprising stable glycerin-in-oil and oil-in-glycerin Pickering-type emulsions which include magnesium stearate as the sole emulsifier, as well as methods of manufacturing the same. As explained herein, the stable emulsions according to this aspect of the disclosure have improved stability compared to traditional glycerin and oil emulsions. In some aspects, compositions presented herein range in viscosity from about 1,000 to about 250,000 centipoise ("cP"). For example, compositions prepared according to the present disclosure may have a viscosity of about, at least, or at most 1,000; 2,000; 3,000; 4,000; 5,000; 6,000; 7,000; 8,000; 9,000; 10,000; 11,000; 12,000; 13,000; 14,000; 15,000; 16,000; 17,000; 18,000; 19,000; 20,000; 25,000; 30,000; 35,000; 40,000; 45,000; 50,000; 60,000; 70,000; 80,000; 90,000; 100,000; 110,000; 120,000; 130, 000; 140,000; 150,000; 160,000; 170,000; 180,000; 190,000; 200,000, 210,000; 220,000; 230,000; 240,000; or 250,000 cP (or a viscosity within a range bounded by any of these values).

In some aspects, compositions according to the invention may have decreased viscosity when exposed to high temperatures 49-60° C., with viscosity increasing to the original level upon cooling to room temperature. Compositions prepared according to the disclosure without thickeners may exhibit some form of flocculation after storage for several days at 60° C. However, internal phase droplets show no sign of coalescence, maintaining their original size and integrity. The flocculation that does occur is easily reversible with agitation and does not constitute degradation.

In some aspects, emulsions prepared according to the disclosure have improved stability as compared to other glycerin and oil emulsions made with known methods and materials. Stability is commonly measured in the cosmetic arts by a variety of methods that observe changes in viscosity, pH, color, visual texture, etc. Usual stability testing includes challenging the formulations at a variety of thermal extremes to determine shelf life for retail purposes, as all emulsions are thermodynamically unstable this is a method to estimate long term stability. For example, typical tests include heating the composition to 45° C. for overnight, 1 week, 2 weeks, 4 weeks, 8 weeks, and the like. Alternatively, heating the compositions to more extreme temperatures including 49° C. and 60° C., as well as subjecting the composition to several freeze-thaw-cycles to mimic any transient conditions they may encounter during its lifetime. In some aspects, stability may be tested by subjecting the compositions to about 60° C. for 12 hours, 24 hours, and 168 hours; about 49° C. for 24 hours, 1 week, 2 weeks, 4 weeks, and 8 weeks; as well as four 12 hour freeze-thaw cycles using temperatures of about −2° C. and 25° C. Evaluation of stability after several such storage conditions was performed qualitatively by visual inspection by naked eye and/or with the aid of an optical microscope. In some aspects, there was no visible separation of phases only mild flocculation as observed by 1000× magnification using an optical microscope.

All amounts provided in terms of weight percentage herein are relative to the entire emulsion, including both the internal phase and the external phase unless otherwise stated. It will be understood that the total of all weight percentages in a given composition will not exceed 100%.

Furthermore, the term "anhydrous," as used herein, refers to a composition in which no water is added but which may include trace amounts of moisture adsorbed or absorbed from the atmosphere not to exceed 1% by weight of glycerin. Trace amounts of moisture may be found even in USP glycerin, which comprises approximately 99.52% glycerin with only 0.23% water content as per typical analysis.

The emulsions of the present disclosure are generally glycerin-in-oil emulsions comprising a discontinuous, internal glycerin phase and a continuous, external oil phase. The internal phase may comprise, e.g., from about 5% to about 75% by weight of the entire emulsion. In some aspects, the internal phase will comprise from about 15% to about 30% by weight of the entire emulsion. In some aspects the internal phase may comprise at least, at most, or about 5, 15, 25, 35, 45, 55, 65, or 75% by weight of the entire emulsion). In some aspects, the internal phase may comprise an amount in a range having endpoints selected from any of the aforementioned values (e.g., 15-35% or 55-65% by weight of the entire emulsion).

The external phase will typically comprise from about 70% to about 85% by weight of the entire emulsion. In some aspects, the external phase will comprise from about 55% to about 85% by weight of the entire emulsion. In some aspects, the external oil phase may comprise 25-95% by weight of the entire emulsion (e.g., at least, at most, or about 25, 35, 45, 55, 65, 75, 85, or 95% by weight of the entire emulsion). In some aspects, the external oil phase may comprise an amount in a range having endpoints selected from any of the aforementioned values (e.g., 25-35% or 45-65% by weight of the entire emulsion).

In alternative embodiments, emulsions according to the disclosure may comprise oil-in-glycerin emulsions comprising a discontinuous, internal oil phase and a continuous, external glycerin phase. The internal phase can comprise, e.g., from about 5% to about 65% by weight of the entire emulsion (e.g., at least, at most or exactly 5, 15, 25, 35. 45, 55 or 65% % by weight of the entire emulsion). The internal phase may alternatively comprise an amount within a range bounded by any of these values. In some aspects, the internal phase will comprise from about 15% to about 30% by weight of the entire emulsion. The external phase may comprise, e.g., from about 35% to about 95% by weight of the entire emulsion (e.g., at least, at most or about 35, 45, 55, 65, 75, 85 or 95% by weight of the entire emulsion. The external phase may alternatively comprise an amount within a range bounded by any of these values In some exemplary aspects, the external phase will comprise from about 55% to about 85% by weight of the entire emulsion.

In some exemplary aspects, glycerin is used as the main component of the polar phase. However, other polyols may be substituted in place of or in addition to glycerin, e.g., ethylene glycol, propylene glycol, butylene glycol, hexylene glycol, sorbitol, and diethylene glycol. Suitable polyols for inclusion in the internal phase further include, without limitation, $C_{2-6}$ polyols such as ethylene glycol, propylene glycol, butylene glycol, hexylene glycol, sorbitol, diethylene glycol. It is understood that an emulsion according to the disclosure may be formulated according to any aspect described herein with any of these alternative polyols included in place of glycerin, within the amounts and/or ranges described as for glycerin.

As used herein, the term "oil" is used to mean any oil including vegetable oils, plant oils, nut oils, fruit oils, seed oils, any hydrocarbon oil, and mineral or synthetic. The oil phase of the compositions described herein may comprise any suitable oils for emulsions, including, without limitation, vegetable oils; fatty acid esters; fatty alcohols; isoparaffins such as isododecane and isoeicosane; hydrocarbon oils such as mineral oil, petrolatum, and polyisobutene; polyolefins and hydrogenated analogs; natural or synthetic waxes; silicone oils such as dimethicones, cyclic silicones, and polysiloxanes; and the like.

As indicated above, the oil may comprise one or more fatty acid esters. Special mention may be made of those esters commonly used as emollients in cosmetic formulations. Such esters will typically be the etherification product of an acid of the form $R_4(COOH)_{1-2}$ with an alcohol of the form $R_5(OH)_{1-3}$ where $R_4$ and $R_5$ are each independently linear, branched, or cyclic hydrocarbon groups, optionally containing unsaturated bonds (e.g., from 1-6 or 1-3 or 1), and having from 1 to 30 (e.g., 6-30 or 8-30, or 12-30, or 16-30) carbon atoms, optionally substituted with one or more functionalities including hydroxyl, oxa, oxo, and the like. Preferably, at least one of $R_4$ and $R_5$ comprises at least 8, or at least 10, or at least 12, or at least 16 or at least 18 carbon atoms, such that the ester comprises at least one fatty chain. The esters defined above will include, without limitation, the esters of mono-acids with mono-alcohols, mono-acids with diols and triols, di-acids with mono-alcohols, and tri-acids with mono-alcohols. Suitable fatty acid esters include, without limitation, butyl acetate, butyl isostearate, butyl oleate, butyl octyl oleate, cetyl palmitate, ceyl octanoate, cetyl laurate, cetyl lactate, cetyl isononanoate, cetyl stearate, diisostearyl fumarate, diisostearyl malate, neopentyl glycol dioctanoate, dibutyl sebacate, di-$C_{12-13}$ alkyl malate, dicetearyl dimer dilinoleate, dicetyl adipate, diisocetyl adipate, diisononyl adipate, diisopropyl dimerate, triisostearyl trilinoleate, octodecyl stearoyl stearate, hexyl laurate, hexadecyl isostearate, hexydecyl laurate, hexyldecyl octanoate, hexyldecyl oleate, hexyldecyl palmitate, hexyldecyl stearate, isononyl isononanaote, isostearyl isononate, isohexyl neopentanoate, isohexadecyl stearate, isopropyl isostearate, n-propyl myristate, isopropyl myristate, n-propyl palmitate, isopropyl palmitate, hexacosanyl palmitate, lauryl lactate, octacosanyl palmitate, propylene glycol monolaurate, triacontanyl palmitate, dotriacontanyl palmitate, tetratriacontanyl palmitate, hexacosanyl stearate, octacosanyl stearate, triacontanyl stearate, dotriacontanyl stearate, stearyl lactate, stearyl octanoate, stearyl heptanoate, stearyl stearate, tetratriacontanyl stearate, triarachidin, tributyl citrate, triisostearyl citrate, tri-$C_{12-13}$-alkyl citrate, tricaprylin, tricaprylyl citrate, tridecyl behenate, trioctyldodecyl citrate, tridecyl cocoate, tridecyl isononanoate, glyceryl monoricinoleate, 2-octyldecyl palmitate, 2-octyldodecyl myristate or lactate, di(2-ethylhexyl)succinate, tocopheryl acetate, and the like. Other suitable esters include those wherein $R_5$ comprises a polyglycol of the form H—(O—CHR*—CHR*)$_n$— wherein R* is independently selected from hydrogen or straight chain $C_{1-12}$ alkyl, including methyl and ethyl, as exemplified by polyethylene glycol monolaurate.

Emulsions according to the disclosure may also comprise hydrocarbon oils. Exemplary hydrocarbon oils are straight or branched chain paraffinic hydrocarbons having from 5 to 80 carbon atoms, typically from 8 to 40 carbon atoms, and more typically from 10 to 16 carbon atoms, including but not limited to, pentane, hexane, heptane, octane, nonane, decane, undecane, dodecane, tetradecane, tridecane, and the like. Some useful hydrocarbon oils are highly branched aliphatic hydrocarbons, including $C_{8-9}$ isoparaffins, $C_{9-11}$ isoparaffins, $C_{12}$ isoparaffin, $C_{20-40}$ isoparaffins and the like. Special mention may be made of the isoparaffins having the INCI names isohexadecane, isoeicosane, and isododecane (IDD). Also suitable as hydrocarbon oils are poly-alpha-olefins, typically having greater than 20 carbon atoms, including (optionally hydrogenated) $C_{24-28}$ olefins, $C_{30-45}$ olefins, polyisobutene, hydrogenated polyisobutene, hydrogenated polydecene, polybutene, hydrogenated polycyclopentane, mineral oil, pentahydrosqualene, squalene, squalane, and the like. The hydrocarbon oil may also comprise higher fatty alcohols, such as oleyl alcohol, octyldodecanol, and the like.

Other suitable oils include without limitation castor oil, $C_{10-18}$ triglycerides, caprylic/capric/triglycerides, argan oil, shea butter, mango butter, cocoa butter, coconut oil, corn oil, cottonseed oil, linseed oil, mink oil, olive oil, palm oil, illipe butter, rapeseed oil, hemp seed oil, rosehip oil, soybean oil, sunflower seed oil, walnut oil, avocado oil, camellia oil, macadamia nut oil, turtle oil, mink oil, soybean oil, grape seed oil, sesame oil, maize oil, rapeseed oil, pomegranate seed oil, cranberry seed oil, sunflower oil, cottonseed oil, jojoba oil, peanut oil, olive oil, and combinations thereof To increase stability of an emulsion, according to Stokes' Law (as shown in Equation 1), one may (1) increase the viscosity of the external phase, (2) decrease internal phase droplet size, and (3) decrease the difference in density of the two phases.

$$V = \frac{2a^2(\rho_i - \rho_e)g}{9\eta} \qquad \text{(Eq. 1, Stokes' Law)}$$

Where a is the droplet size, $\rho_i$ is the density of the internal phase, $\rho_e$ is the density of the external phase, g is the acceleration due to gravity, and $\eta$ is the viscosity of the external phase.

Due to the fact the glycerin and oil have much more disparate densities (1.26-0.93 g/mL) than water and oil (1.00-0.93 g/mL), glycerin and oil emulsions are inherently more unstable than oil and water emulsions. Typical glycerin-in-oil emulsions using standard emulsifiers create non-stable emulsions with average internal phase droplet sizes in the ~100 µm range. Without being bound to a theory, the Pickering emulsions according to some aspects of the disclosure are believed to comprise emulsions with smaller average internal phase droplets (e.g., in the ~0.9 µm range range) which yield increased stability. Exemplary droplet sizes include e.g., about, at least or approximately 100, 200, 300, 400, 500, 600, 700, 800, 900, or 950 nm (or a size within a range bounded by any of these values). In some aspects, when emulsions are prepared accorded to the present disclosure using (1) sorbitan olivate as the emulsifier or (2) magnesium stearate and sorbitan olivate as co-emulsifiers, the droplets may have a larger average diameter of 10-30 µm, e.g., about, at least or approximately 10, 11, 12, 13, 14, 15, 16, 17, 18, 19, 20, 21, 22, 23, 24, 25, 26, 27, 28, 29, or 30 µm (or a size within a range bounded by any of these values). In some exemplary aspects, waxes may be added to increase the viscosity of the external phase leading to increased thickness and potentially increased stability of the emulsions. In some aspects, emulsions according to the disclosure do not include any waxes.

Additional components may be incorporated for various functional purposes as is customary in the cosmetic arts into the internal phase, the external phase, or as a particulate phase. However, while additional components consistent to formulate the above cosmetic compositions may be included, the inclusion of additional ingredients is limited to those ingredients in amounts which do not interfere with the formation or stability of the glycerin-in-oil emulsion.

Emulsions according to the disclosure are well-suited for cosmetic and pharmaceutical compositions for topical application. When formulated in this manner, the emulsions will typically include additional components that may or may not be included in either the continuous or discontinuous phase. Said components may consist of botanicals, emollients, antioxidants, vitamins, waxes, soaps, and any combination thereof. These additional components may be added for aesthetic characteristics such as opacity, color, pearlescence, texture and feel. Some aspects may contain tocopherol in the continuous phase, as natural botanical oils tend to go rancid without it. Additional aspects may contain other antioxidants to impart additional functionality. Furthermore, the emulsions according to the disclosure may be used as a delivery system for notoriously unstable actives such as L-ascorbic acid and resveratrol which are oxidized in the presence of water.

When formulated as face creams, the emulsions according to the invention may be packaged in a variety of containers, however, only reclosable glass jars will be used in accordance with our green, sustainable practices. When formulated as lip products, the emulsions according to the invention may be packaged in glass jars, as envisioned for lip gloss, or metal lipstick containers, as envisioned for a more solid, waxy lip product.

Additional components may be incorporated for various other functional purposes and aesthetics as is frequent in the cosmetic arts.

The following non-limiting examples illustrate aspects of the present disclosure.

Example 1: General Methods

The compositions described in Examples 2-6 below were made using the following method, which utilizes a rapid cooldown and an optional temperature shock step not found in known methods for producing stable emulsions comprising glycerin and oil.

Step 1: Heat the oil phase, any wax(es), and emulsifier(s) to about 85° C. These components may optionally be heated together after addition to the oil phase or heated separately and added to the oil phase. If magnesium stearate is to be used as an emulsifier, add the magnesium stearate to the oil phase at high shear (and optionally, without heating).

Step 2: Separately, heat the glycerin phase to 85° C.

Step 3: While mixing the oil phase at high shear, add the glycerin phase to the oil phase to form an emulsion.

Step 4: After mixing for ~30 seconds, transfer the mixing vessel containing the emulsion to a cold water bath or other source of refrigeration (e.g., at 0° C.). In some aspects, alternative temperatures may be used to rapidly cool down the emulsion (e.g., 0, 1, 2, 3, 4, or 5° C., or a temperature within a range bounded by any of these values). In some aspects, mixing may proceed for at least, about, or at most 10, 15, 20, 25, 30, 35, 40, 45, 50, 55, or 60 seconds, or within a time range bounded by any of these values).

Step 5: If using sorbitan olivate as the sole or a co-emulsifier, a portion of the oil phase (e.g., 1, 2, 3, 4, 5, 6, 7, 8, 9, 10, 11, 12, 13, 14, 15, 16, 17, 18, 19, or 20%) may be added to the chilled emulsion at or after step 4 (e.g., at 0° C.). This step is optional and may decrease the size of internal phase droplets by a small degree.

Step 6: Mix the emulsion under high shear for about 3 minutes or until the temperature reaches 35-45° C., or optionally, until the composition has a desired pouring thickness. In some aspects, mixing may proceed for at least, about, or at most 1, 2, 3, 4, 5, 6, 7, 8, 9, or 10 minutes, or for an amount of time within a range bounded by any of these values. Similarly, in some aspects mixing may proceed until the temperature reaches at least, about, or at most 35, 36, 37, 38, 39, 40, 41, 42, 43, 44, or 45° C., or for a duration of time within a range bounded by any of these values.

Alternatively, emulsions described herein may also be prepared using methods known in the art, for example by mixing at high shear for 30 minutes until natural cooldown is achieved. In addition, as the emulsifier is used for Pickering-type emulsions, emulsions may also be prepared cold as long as no optional components used need to be melted into a particular phase.

Example 2: Stability of Magnesium Stearate Compared to Conventional Emulsifiers

For comparative purposes, most formulations described herein were made according to the general recipe shown in Table 1 (i.e., using "Formulation A"). Table 2 shows the stability of glycerin-in-oil emulsions according to Formula A which include traditional emulsifiers. As noted above, glycerin-in-oil emulsions produced according to known methods are not considered to be stable. All of the tested formulations, using several emulsifiers and a range of hydrophilic-lipophilic balance (HLB) values, 4.7-15.5, were unstable. None of the formulations embodied in Examples 1-7 would be suitable for cosmetic use. All HLB values described in this experiment were calculated using Equation 2, shown below.

$$HBL = (\Sigma m_{oil} HLB_{oil}) / \Sigma m_{oil} \quad \text{(Eq. 2)}$$

where $m_{oil}$ is the mass of the oil and $HLB_{oil}$ is the HLB value of the given oil.

TABLE 1

Ingredients used for test Formulation A. The HLB value of Formulation A is around 9.1.

| Formulation A | Amount (% w/w) |
|---|---|
| Glycerin | 25.0 |
| Macadamia Nut Oil | 46.0 |
| Castor Oil | 21.5 |
| Shea Butter | 4.5 |
| Emulsifier | 3.0 |

TABLE 2

Stabilities of glycerin-in-oil emulsions using standard emulsifiers in combination to test a range of HLB values. All examples were prepared as the basic Formulation A, with varying amounts of emulsifiers totaling to 3.0% by weight. Stability ratings range from 0-5. A temperature of 25° C. was maintained for all examples.

| Ex. | Cetearyl Alcohol | Sorbitan Stearate | Stearic Acid | HLB | Stability Rating | Separation Time | Stability |
|---|---|---|---|---|---|---|---|
| Ex. 1 | — | 3.0 | — | 4.7 | 0 | minutes | Not Stable |
| Ex. 2 | 0.64 | 2.36 | — | 7.0 | 1 | <hour | Not Stable |
| Ex. 3 | 1.23 | 1.77 | — | 9.14 | 2 | 1-2 hours | Not Stable |
| Ex. 4 | 2.03 | 0.97 | — | 12.0 | 1 | <hour | Not Stable |
| Ex. 5 | 3.0 | — | — | 15.5 | 0 | minutes | Not Stable |
| Ex. 6 | — | 2.30 | 0.70 | 7.10 | 1 | <hour | Not Stable |
| Ex. 7 | — | 1.70 | 1.30 | 9.16 | 2 | 1-2 hours | Not Stable |

A combination of emulsifiers in conjunction with magnesium stearate were also tested for stability. In the tested examples, e.g., Examples 8-10 as shown in Table 3, the addition of traditional emulsifiers did not add to the stability of the formulation. On the contrary, the formulations were less stable than just using magnesium stearate as the sole emulsifier. The only exception being Example 11, the formulation which used sorbitan olivate, (sold commercially as Olivem® 900), as a co-emulsifier. Without being bound to a theory, it is believed that magnesium stearate and sorbitan olivate may interact synergistically to stabilize Pickering emulsions, e.g., when present in amounts within the ranges described herein.

TABLE 3

Formulation stability of glycerin-in-oil Pickering-type emulsions using magnesium stearate and/or a combination of traditional emulsifiers. All examples were prepared as the basic Formulation A, with varying amounts of emulsifiers totaling 3.0% w/w. Examples were examined after 1 hour, 2 hours, 12 hours, 24 hours, 36 hours, and 48 hours at 60° C.

| | Magnesium Stearate | Sorbitan Stearate | Stearic Acid | Cetearyl Alcohol | Sorbitan Olivate | Visible Separation |
|---|---|---|---|---|---|---|
| Ex. 8 | 3.0 | — | — | — | — | 48 hours |
| Ex. 9 | 2.0 | 0.57 | — | 0.43 | — | 36-48 hours |
| Ex. 10 | 2.0 | 0.57 | 0.43 | — | — | 12-24 hours |
| Ex. 11 | 2.0 | — | — | — | 1.0 | 48 hours |

Figure 2:
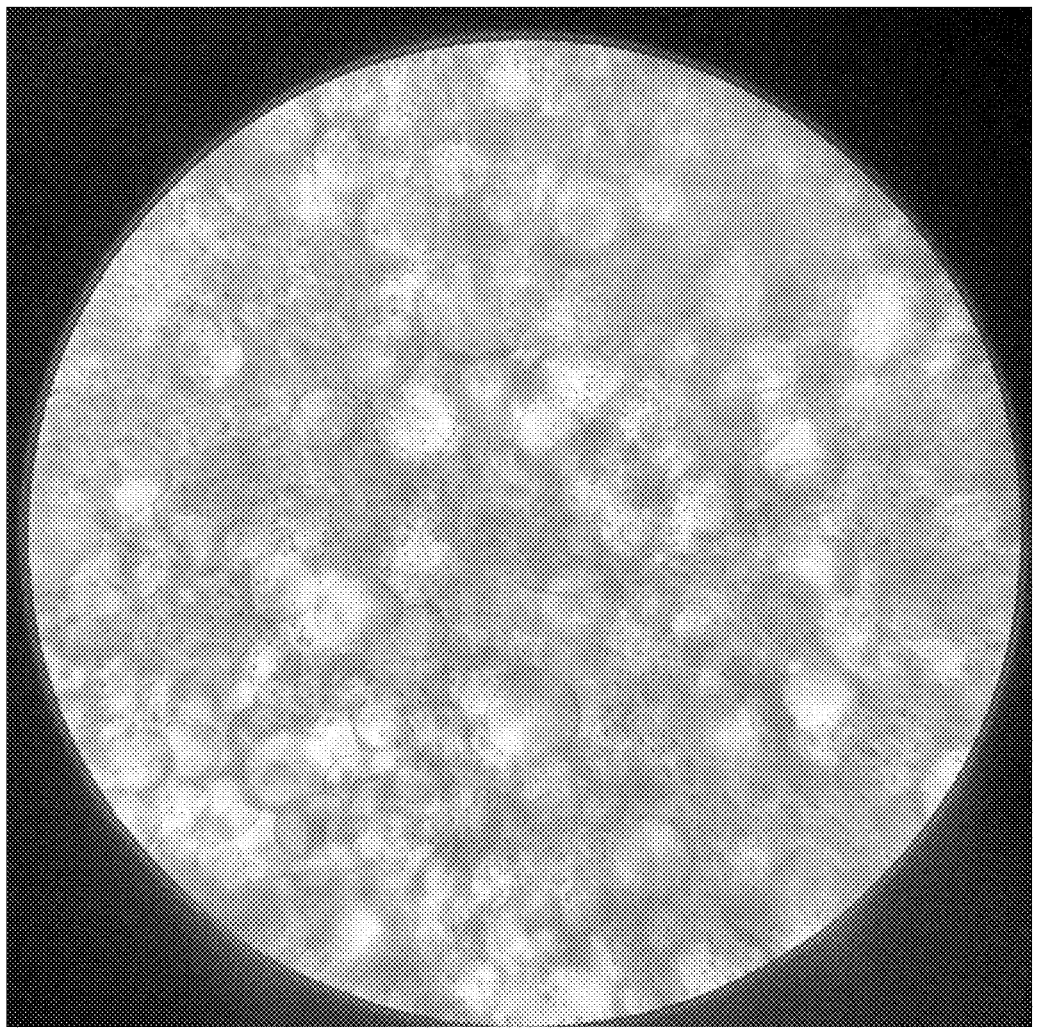
FIG. 2 is a microscope image of Formulation A using 2.0% (w/w) magnesium stearate and 1.0% (w/w) sorbitan olivate as co-emulsifiers (as described in Example 11), viewed at 1000× magnification. The diameter of the field of view is approximately 180 μm.
Figure 3:
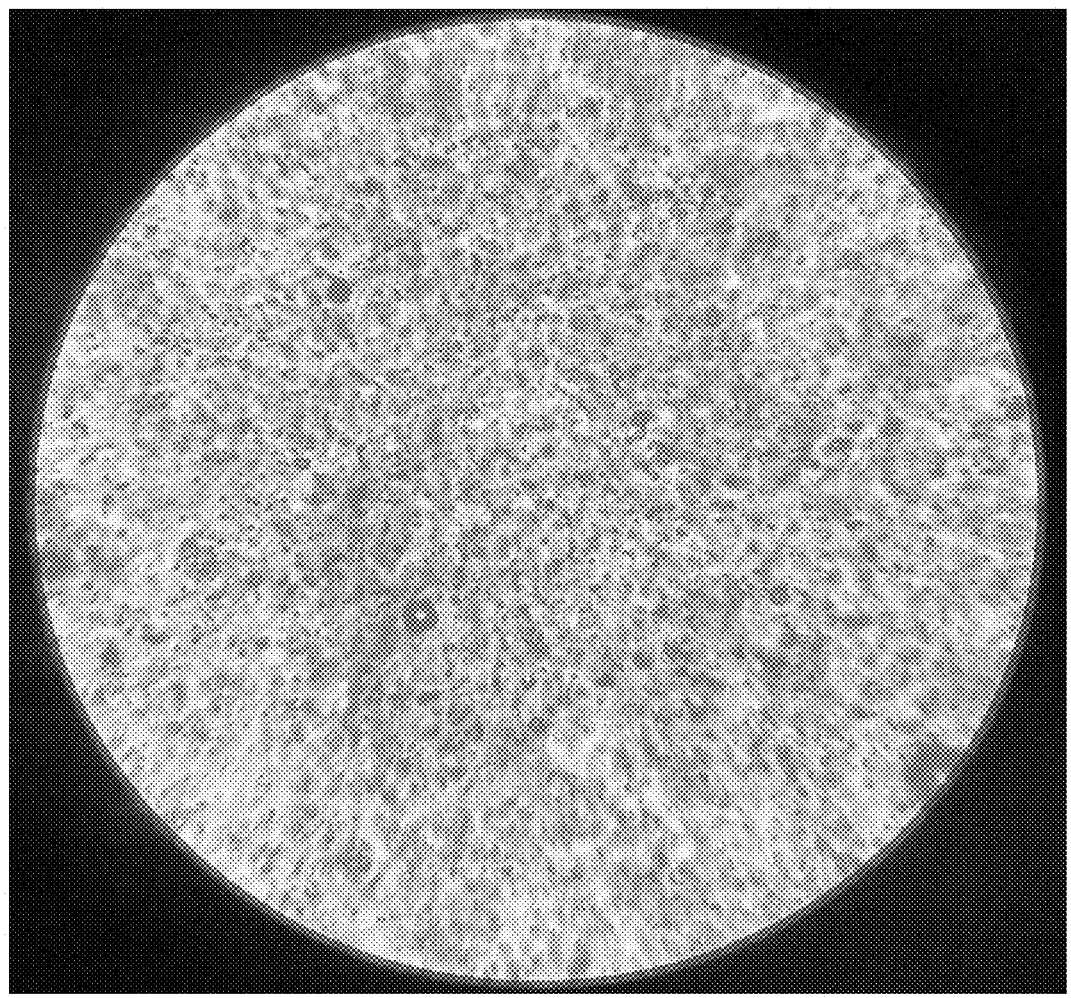
FIG. 3 is a microscope image of Formulation A using 3.0% (w/w) magnesium stearate as the sole emulsifier (as described in Example 12), viewed at 1000× magnification. The diameter of the field of view is approximately 180 μm.

Sorbitan olivate is different than other surfactants as that it typically forms liquid crystals and higher order micelle structures compared to other surfactants However, under microscopic inspection, the internal phase droplets were spherical in nature and of the order of 10-40 microns as shown in FIG. 1. In contrast, formulations using solely magnesium stearate have geometric internal phase droplets on the order of hundreds of nanometers as shown in FIG. 2. The stability of Example 11, is therefore believed to be attributed to sorbitan olivate's ability to increase the viscosity of the continuous phase and/or a synergistic effect observed wherein different geometric shapes are formed in at least some of the internal phase droplets. Formulations made with sorbitan olivate are noticeably thicker than other formulations without added thickeners or viscosity modifiers. Even though, the addition of sorbitan olivate to a formulation with magnesium stearate has increased stability compared to other formulations using co-emulsifiers, further increases in stability can be achieved by adding thickeners like waxes. However, as noted above, the inclusion of thickeners is undesirable for certain applications, e.g., which require a more liquid or liquid-like consistency.

Example 3: Stability of Magnesium Stearate Opposed to Similar Salts

Several formulations using different soaps were also tested for stability against magnesium stearate, including calcium stearate, zinc stearate, sodium stearate, and magnesium palmitate as shown in Table 4. All of the tested formulations, i.e., Examples 13-16, were unstable as the different salts failed to act as emulsifiers. Magnesium stearate, used in Example 12, was found to be the only salt capable of making stable glycerin-in-oil and oil-in-glycerin Pickering-type emulsions. Stability was measured after 48 hours at 60° C. and after about 6 months at room temperature. No separation was observed in either case.

TABLE 4

Comparison of different possible Pickering emulsifiers within similar groups. All tests were done at 25° C. All emulsifiers made up 3.0% w/w of basic Formulation A. Rank stability (1 being the most stable; 5 the least.) was assigned to compare the different compounds relative to each other (i.e., not as a judgement on overall stability).

| Ex. | Emulsifier | Visible Separation | Stability Rating Rank |
|---|---|---|---|
| Ex. 12 | Magnesium Stearate | <6 months | 1 |
| Ex. 13 | Calcium Stearate | minutes | 3 |
| Ex. 14 | Zinc Stearate | <hour | 2 |
| Ex. 15 | Sodium Stearate | minutes | 4 |
| Ex. 16 | Magnesium Palmitate | minutes | 5 |

Example 4: Stability of Magnesium Stearate in Conjunction with Thickeners

Formulations using magnesium stearate as the sole emulsifier and additional thickeners were also explored for stability as shown in Table 5. In all examples, adding thickeners to the continuous phase resulted in a formulation with increased stability as tested at 60° C.

TABLE 5

Results of adding thickeners to the relative stability of Pickering-type emulsions using 2% w/w magnesium stearate as the sole emulsifier of basic Formulation A. All amounts are given in % (w/w) based on the total emulsion. For the examples involving castor wax or carnauba, the amount of macadamia nut oil was reduced and in the examples involving arrowroot or agar, the amount of glycerin was reduced. All of the tested emulsions were subjected to 60° C.

| Ex. | Castor Wax | Carnauba Wax | Arrowroot Starch | Agar | Visible Leeching |
|---|---|---|---|---|---|
| Ex. 17 | 2.0 | — | — | — | 48 hours |
| Ex. 18 | 3.0 | — | — | — | 6 days |
| Ex. 19 | 4.0 | — | — | — | >1 week |
| Ex. 20 | — | 1.0 | — | — | 48 hours |
| Ex. 21 | — | 2.0 | — | — | >1 week |
| Ex. 22 | — | 1.0 | 1.0 | — | 6 days |
| Ex. 23 | — | 1.0 | — | 0.4 | 36 hours |

As illustrated by Table 5, adding thickeners to the internal glycerin phase resulted in mixed results. Incorporating arrowroot powder to the internal phase, Example 22, resulted in a formulation that was stable at 60° C. for 4 days longer than a formulation lacking this element, i.e., Example 22. Conversely, the addition of agar to the internal glycerin phase, example 23, resulted in decreased stability of the overall formulation. Therefore, it is evident that adding thickeners to the internal phase may or may not increase the stability of formulations depending on the characteristics of said thickeners.

Example 5: The Addition of Water to the Internal Glycerin Phase on the Stability of Formulations The addition of adding water to the internal glycerin phase was also explored to evaluate whether this variable impacts stability. In Example 18 of Table 5, 5% glycerin was replaced with distilled water and prepared as usual. The addition of water resulted in an emulsion with slightly increased thickness and a slight increase in stability, as measured by a few more hours at 60° C. without visible separation than the formulation without additional water. This is not a surprising result as the addition of water decreases the density of the glycerin phase decreasing the amount of Stokes settling as highlighted in Equation 1.

Example 6: Oil-in-Glycerin Emulsions

An oil-in-glycerin formulation was also prepared using a basic formulation comprising 72% glycerin, 25% macadamia nut oil, and 3% magnesium stearate. This basic formulation was prepared using the method described in Example 1, the differences being that magnesium stearate was added to the glycerin phase under constant shear followed by the addition of the oil to the glycerin phase. All other steps of the procedure were the same. The formulation was much more stable than the glycerin-in-oil formulations. The resulting emulsion was a very thick gel that did not exhibit any visible phase separation after being subjected to 60° C. for 1 week. This result is most likely due to the viscosity of glycerin. As glycerin, in this embodiment, is in the continuous phase increased viscosity adds to the stability of emulsions as per Stokes' equation.

As used herein, the terms "comprising," "including," "containing," "characterized by," and grammatical equivalents thereof are inclusive or open-ended terms that do not exclude additional, unrecited elements or method acts, but also include the more restrictive terms "consisting of" and "consisting essentially of" and grammatical equivalents thereof. As used herein, the term "may" with respect to a material, structure, feature or method act indicates that such is contemplated for use in implementation of an embodiment of the disclosure and such term is used in preference to the more restrictive term "is" so as to avoid any implication that other, compatible materials, structures, features and methods usable in combination therewith should or must be, excluded.

As used herein, the singular forms "a," "an," and "the" are intended to include the plural forms as well, unless the context clearly indicates otherwise.

As used herein, the term "and/or" includes any and all combinations of one or more of the associated listed items.

All statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

The invention claimed is:

1. A Pickering-type emulsion, comprising:
    a discontinuous internal phase, wherein the internal phase comprises a polyol in an amount of from about 15% to about 30% by weight of the entire emulsion;
    a continuous external oil phase, in an amount of from about 55% to about 85% by weight of the entire emulsion; and
    an emulsifier, wherein the emulsifier comprises magnesium stearate.

2. The Pickering-type emulsion of claim 1, wherein the polyol is selected from the group consisting of ethylene glycol, propylene glycol, butylene glycol, hexylene glycol, sorbitol, and diethylene glycol.

3. The Pickering-type emulsion of claim 1, wherein the polyol is glycerin.

4. The Pickering-type emulsion of claim 1, further comprising sorbitan olivate as a co-emulsifier.

5. The Pickering-type emulsion of claim 1, wherein the discontinuous internal phase comprises spherical droplets having a diameter of 10-40 μm.

6. The Pickering-type emulsion of claim 1, wherein the magnesium stearate is present in an amount of 1-3% by weight of the entire emulsion.

7. The Pickering-type emulsion of claim 6, further comprising sorbitan olivate as a co-emulsifier in an amount of 1-3% by weight of the entire emulsion.

8. The Pickering-type emulsion of claim 7, wherein the emulsion is stable for at least 48 hours at 60° C., displaying no visible phase separation.

9. The Pickering-type emulsion of claim 7, wherein the emulsion is stable for at least 6 months at room temperature, displaying no visible phase separation.

10. The Pickering-type emulsion of claim 1, wherein the magnesium stearate is localized to the interface between the discontinuous internal phase and the continuous external oil phase.

11. A Pickering-type emulsion, comprising:
    a discontinuous internal phase, wherein the internal phase comprises an oil in an amount of from about 5% to about 65% by weight of the entire emulsion;
    a continuous external polyol phase, in an amount of from about 35% to about 95% by weight of the entire emulsion; and
    an emulsifier, wherein the emulsifier comprises magnesium stearate.

12. The Pickering-type emulsion of claim 11, wherein the polyol is selected from the group consisting of ethylene glycol, propylene glycol, butylene glycol, hexylene glycol, sorbitol, and diethylene glycol.

13. The Pickering-type emulsion of claim 11, wherein the polyol is glycerin.

14. The Pickering-type emulsion of claim 11, further comprising sorbitan olivate as a co-emulsifier.

15. The Pickering-type emulsion of claim 11, wherein the discontinuous internal phase comprises spherical droplets having a diameter of 10-40 μm.

16. The Pickering-type emulsion of claim 11, wherein the magnesium stearate is present in an amount of 1-3% by weight of the entire emulsion.

17. The Pickering-type emulsion of claim 16, further comprising sorbitan olivate as a co-emulsifier in an amount of 1-3% by weight of the entire emulsion.

18. The Pickering-type emulsion of claim 17, wherein the emulsion is stable for at least 48 hours at 60° C., displaying no visible phase separation.

19. The Pickering-type emulsion of claim 18, wherein the emulsion is stable for at least 6 months at room temperature, displaying no visible phase separation.

20. The Pickering-type emulsion of claim 11, wherein the magnesium stearate is located at the interface between the discontinuous internal phase and the continuous external polyol phase.

* * * * *